United States Patent
Iversen et al.

(10) Patent No.: US 10,004,611 B2
(45) Date of Patent: Jun. 26, 2018

(54) HAND PROSTHESIS

(71) Applicant: Motion Control, Salt Lake City, UT (US)

(72) Inventors: Edwin Kay Iversen, Salt Lake City, UT (US); Joseph Anthony Jacobs, Salt Lake City, UT (US); Jeffry David Christenson, Salt Lake City, UT (US); Peter Karl Strazdins, Salt Lake City, UT (US); Steven Reese Kunz, Salt Lake City, UT (US); Brent Taylor Jarvis, Salt Lake City, UT (US); Jeff Robert Welch, Salt Lake City, UT (US); Harold Hume Sears, Salt Lake City, UT (US); Arthur David Dyck, Salt Lake City, UT (US)

(73) Assignee: Motion Control, Salt Lake City, UT (US)

( * ) Notice: Subject to any disclaimer, the term of this patent is extended or adjusted under 35 U.S.C. 154(b) by 132 days.

(21) Appl. No.: 15/135,365

(22) Filed: Apr. 21, 2016

(65) Prior Publication Data

US 2016/0235554 A1 Aug. 18, 2016

Related U.S. Application Data

(62) Division of application No. 14/057,916, filed on Oct. 18, 2013, now Pat. No. 9,320,621.
(Continued)

(51) Int. Cl.
*A61F 2/54* (2006.01)
*A61F 2/58* (2006.01)
(Continued)

(52) U.S. Cl.
CPC .............. *A61F 2/586* (2013.01); *A61F 2/583* (2013.01); *A61F 2/68* (2013.01);
(Continued)

(58) Field of Classification Search
CPC .......... A61F 2/583; A61F 2/586; A61F 2/588; A61F 2002/503; A61F 2002/587; B25J 15/083; B25J 15/08; B25J 19/0016
(Continued)

(56) References Cited

U.S. PATENT DOCUMENTS 9,320,621 B2 4/2016 Iversen et al.

FOREIGN PATENT DOCUMENTS

DE 203 01 116 U1 * 3/2003 .............. A61F 2/58
RU 2 110 308 5/1998

* cited by examiner

*Primary Examiner* — David H Willse
(74) *Attorney, Agent, or Firm* — Thorpe North & Western, LLP.

(57) ABSTRACT

A prosthetic hand system may include a plurality of prosthetic fingers and a prosthetic thumb. The prosthetic hand system may include a thumb drive mechanism that may be used to actuate the prosthetic thumb. In some examples, the thumb drive mechanism may be configured to enable the prosthetic thumb to perform a pinching or grasping motion and a release motion. The prosthetic hand system may also include a backlock that enables the prosthetic thumb to maintain pinching or gripping pressure after a motor has been disengaged. The prosthetic hand system may also include a gear lock that may be configured to lock a finger joint. The prosthetic hand system may also include an adaptive gripping joint that may be located on each prosthetic finger. In some examples, the adaptive gripping joint may be configured to passively adapt the plurality of prosthetic fingers to one or more differently shaped objects.

4 Claims, 13 Drawing Sheets

Related U.S. Application Data

(60) Provisional application No. 61/715,763, filed on Oct. 18, 2012.

(51) Int. Cl.
*A61F 2/68* (2006.01)
*B25J 15/00* (2006.01)
*A61F 2/70* (2006.01)
*A61F 2/50* (2006.01)
*A61F 2/76* (2006.01)

(52) U.S. Cl.
CPC . *A61F 2002/503* (2013.01); *A61F 2002/5007* (2013.01); *A61F 2002/5043* (2013.01); *A61F 2002/5072* (2013.01); *A61F 2002/5073* (2013.01); *A61F 2002/5076* (2013.01); *A61F 2002/5096* (2013.01); *A61F 2002/5098* (2013.01); *A61F 2002/587* (2013.01); *A61F 2002/6836* (2013.01); *A61F 2002/6845* (2013.01); *A61F 2002/6854* (2013.01); *A61F 2002/701* (2013.01); *A61F 2002/7635* (2013.01); *B25J 15/0009* (2013.01)

(58) Field of Classification Search
USPC ..................................... 623/63–65
See application file for complete search history.

HAND PROSTHESIS

PRIORITY DATA

This application is a divisional of U.S. patent application Ser. No. 14/057,916, filed Oct. 18, 2013, now U.S. Pat. No. 9,320,621, which claims the benefit of U.S. Provisional Patent Application Ser. No. 61/715,763, filed on Oct. 18, 2012, both of which are incorporated herein by reference.

BACKGROUND

Prostheses (or prosthetics) are artificial devices that replace body parts (e.g., fingers, hands, arms, legs). Generally, prostheses may be used to replace body parts lost by injury or missing from birth. The quality of prostheses has greatly improved in recent years. For example, a prosthetic limb may be molded to have the same shape and density as the person's remaining limb. In addition, silicone skins used to form the prosthetic limb may give the prosthetic limb a life-like appearance. As another example, improvements in prosthetic limbs may allow for increased sensation and movement. However, prosthetic limbs still present numerous challenges, particularly in the area of handling and grasping objects. For example, hand prosthetics may have difficulty in replicating human movements due to the number of different grasps capable by the human hand. In general, these grasps may include the lateral pinch, grasping with the thumb opposed to the fingers, the cylindrical grasp, the power grasp, and/or the handle grasp (also known as the hook and pull).

DETAILED DESCRIPTION

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure are to be considered within the scope of the description.

Figure 1A:
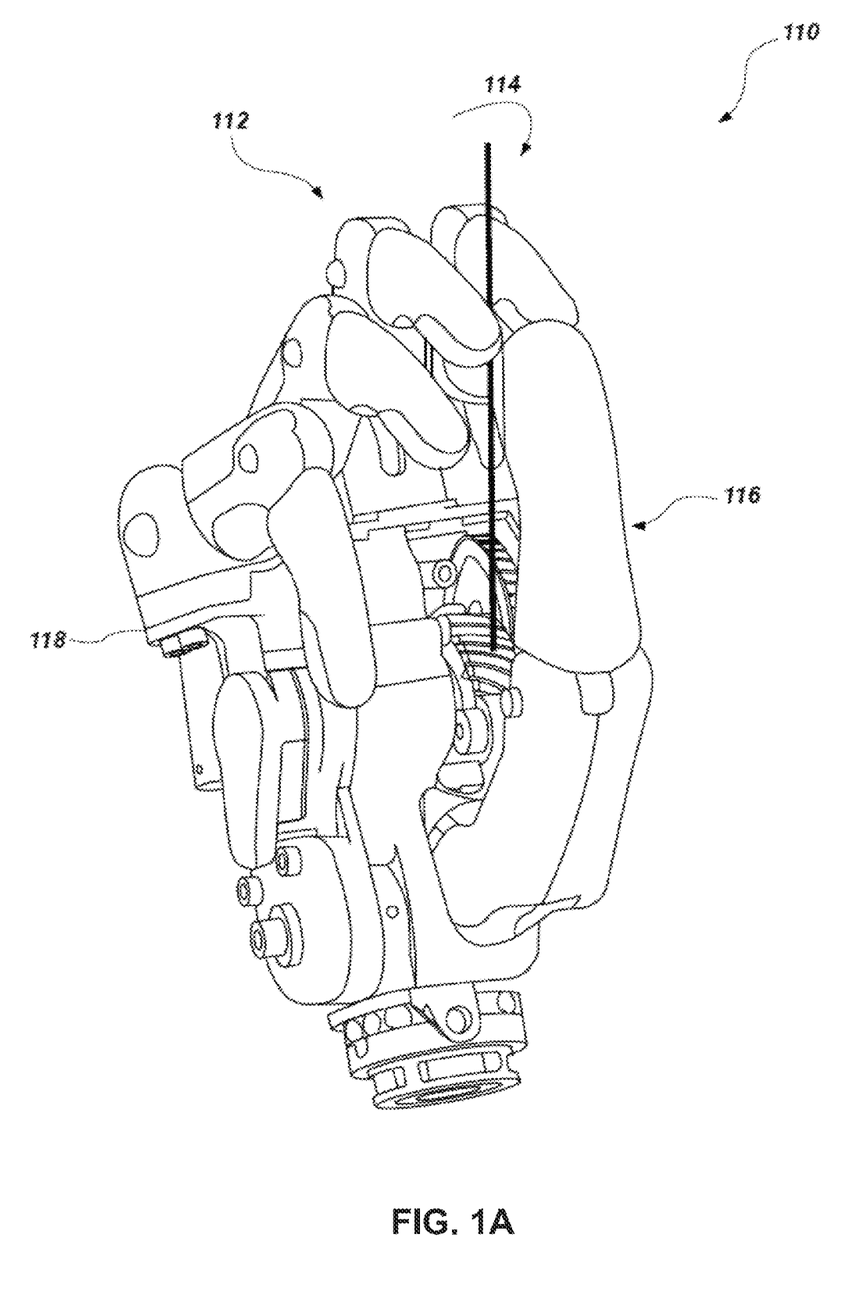
FIGS. 1A-1C show an exemplary hand prosthesis system having a lateral pinch grasping position and a thumb opposition grasping position.
Figure 1B:
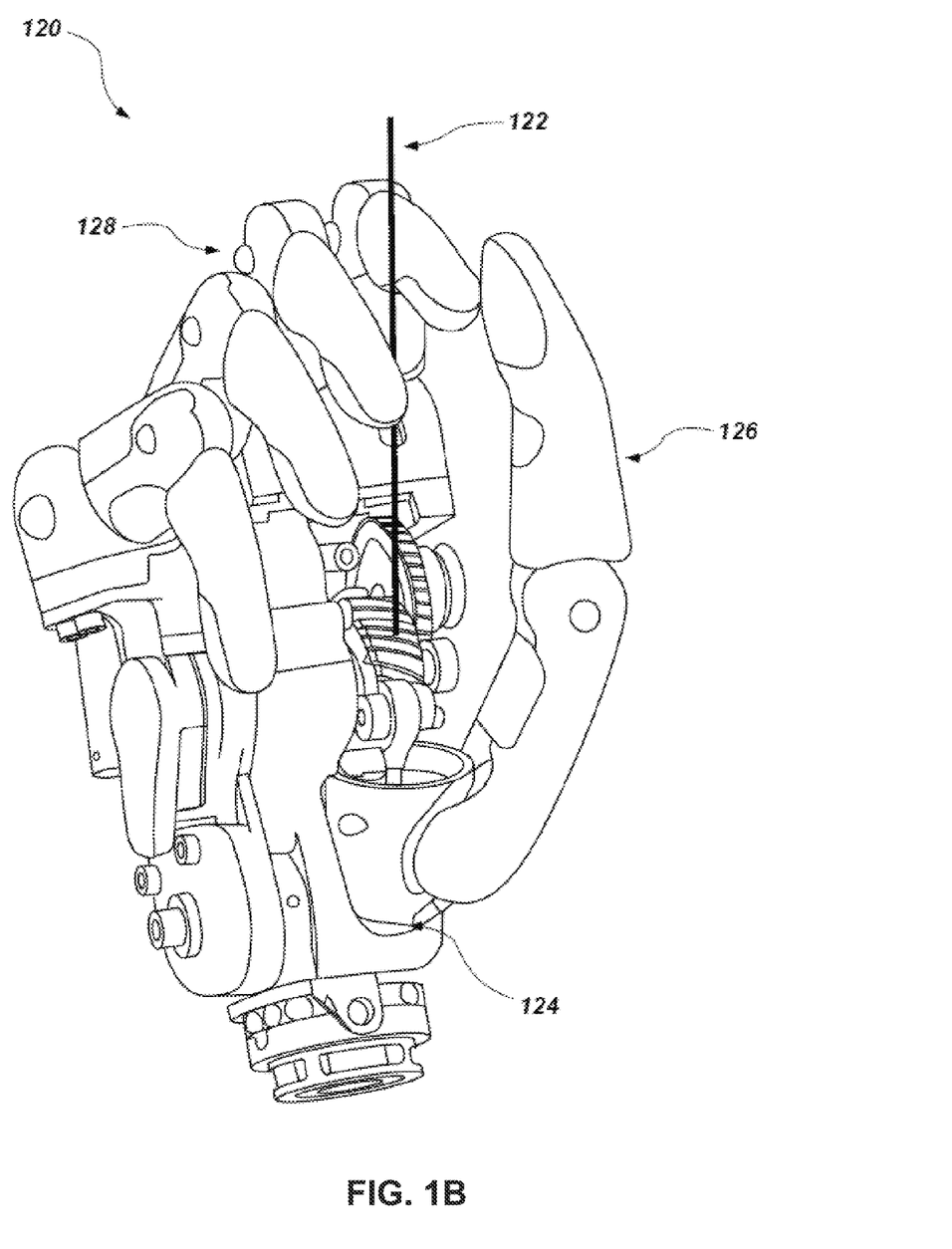
Figure 1C:
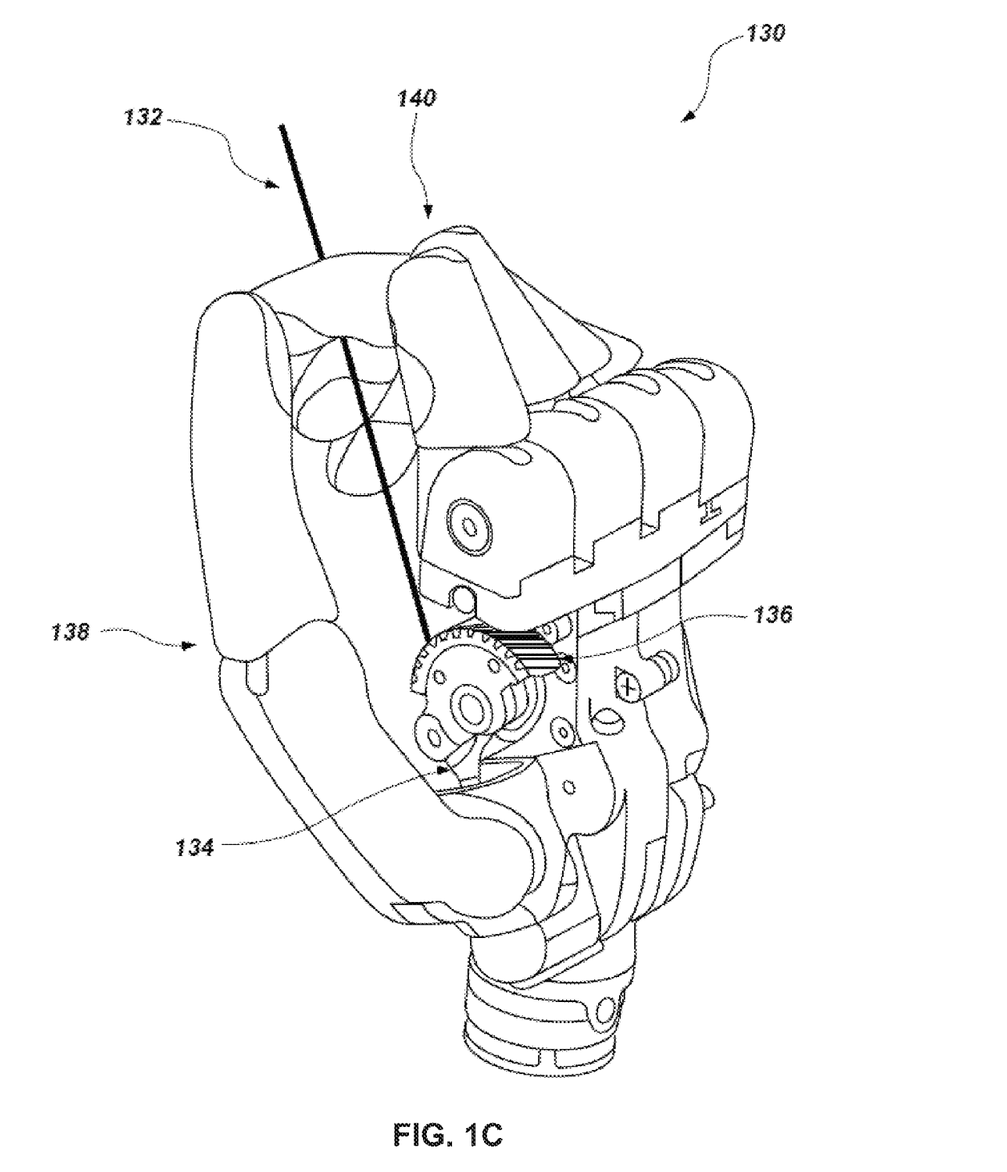

FIGS. 1A-1C illustrate an exemplary hand prosthesis system. The hand prosthetic system 110, 120, and 130 may include an externally-powered hand and wrist prosthetic limb. As used herein, the terms "prosthesis," "prosthetic," and/or "prosthetic limb" are used interchangeably to generally refer to any type or form of artificial limb. FIG. 1A illustrates a hand prosthetic system 110 having a thumb member 116 in opposition to a number of finger members 112 mounted to a hand chassis 118. In addition, the hand prosthetic system 110 may have a thumb axis 114 of rotation.

FIG. 1B illustrates the hand prosthetic system 120 having a thumb member 126 lateral to a number of finger members 128. In one example configuration, the thumb member 126 rotates on a thumb axis 122 to allow the thumb member 126 to rotate from a position where the thumb member 126 is opposite to the finger members 128 (as illustrated in FIG. 1A) to a position where the thumb member 126 is lateral to the finger members 128. In particular, the thumb member 126 may rotate around the thumb axis 114, wherein the thumb axis 114 may intersect the finger-tip area when the finger members 128 are flexed in a common grasping orientation. In one example, the thumb rotation assembly 124 can be configured to enable the thumb member 126 to be moved passively from either a finger opposing position to a finger lateral position or a finger lateral position to a finger opposing position. In another example, a motor can be mounted to a hand chassis 118 and the motor can be connected to a thumb rotation assembly 124 enabling the thumb rotation assembly 124 to rotate on the thumb axis 122 from either a finger opposing position to a finger lateral position or a finger lateral position to a finger opposing position.

FIG. 1C illustrates the hand prosthesis system 130 with a thumb axis 132, which may allow the thumb member 138 to rotate from a thumb opposition grasping position to a lateral pinch grasping position. As shown in FIG. 1C, and as discussed in greater detail below, the hand prosthetic system 130 may include a thumb drive mechanism. In some examples, the thumb drive mechanism may utilize a rod-end bearing 134 and an output gear 136 to enable the thumb member 138 to actuate. In one example, operating the thumb drive mechanism can cause the thumb member 138 to perform a pinching action. Depending upon the position of the thumb member 138 along the thumb axis 132, operating the thumb drive mechanism can produce a pinch gripping action that is lateral to the finger members 140 or a pinch gripping action that is opposing to the finger members 140. In some examples, rotation of the thumb member 138 from the lateral pinch position to the finger opposition position may allow for enhanced grasp for a person using the hand prosthesis system 130.

Figure 2A:
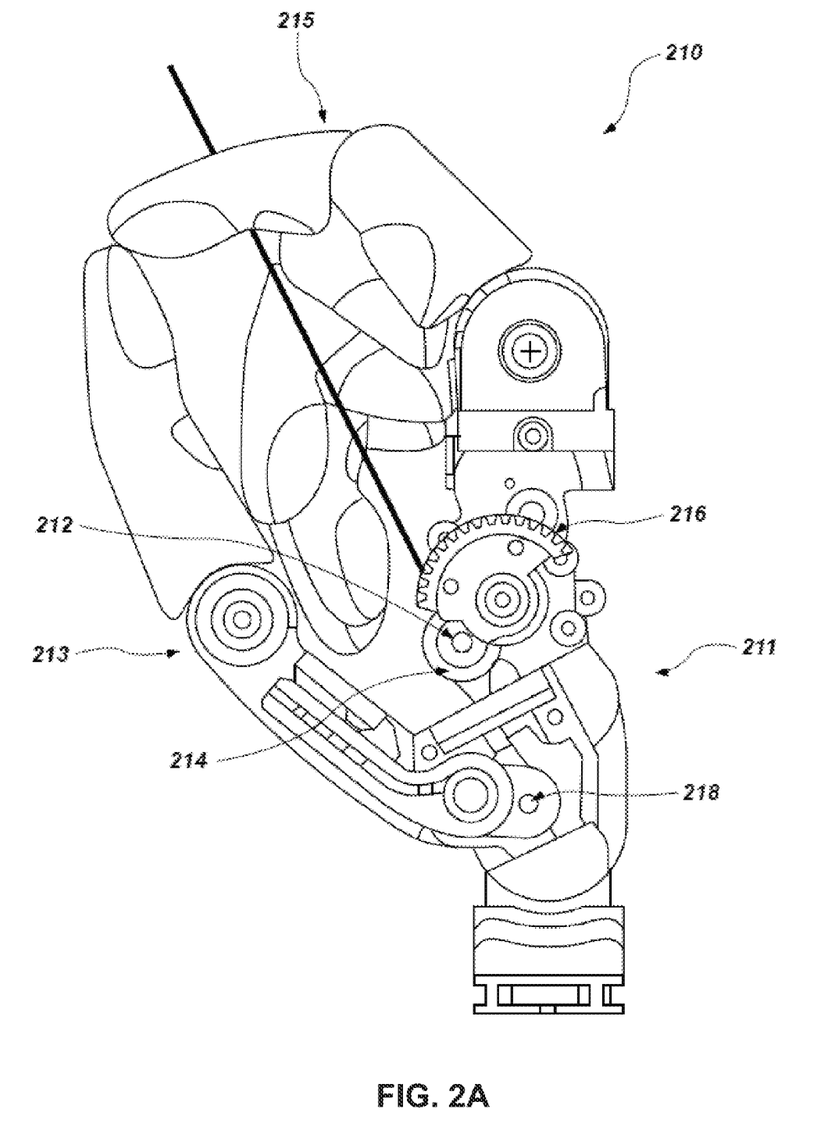
FIGS. 2A-2C show an exemplary thumb drive mechanism included in the hand prosthesis system.
Figure 2B:
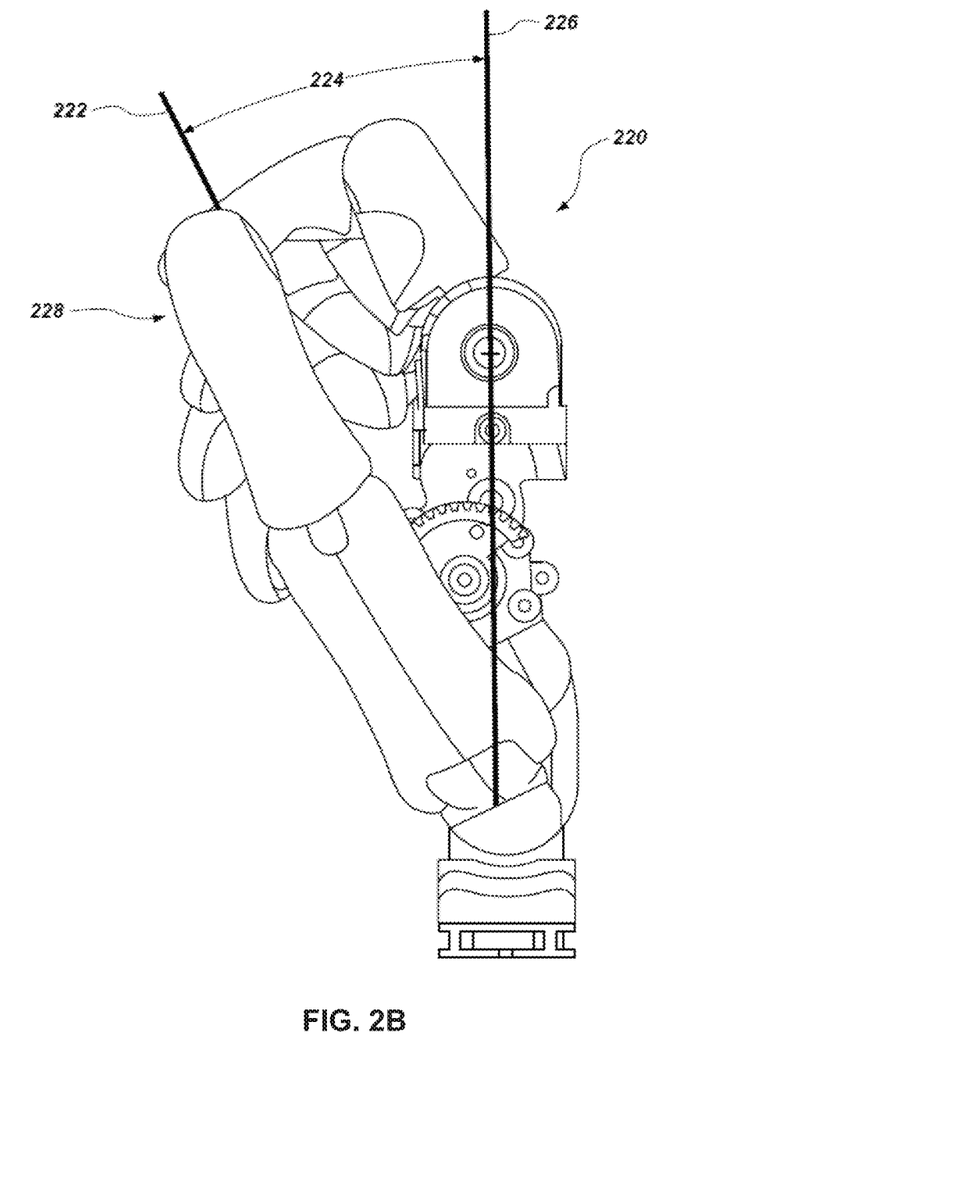
Figure 2C:
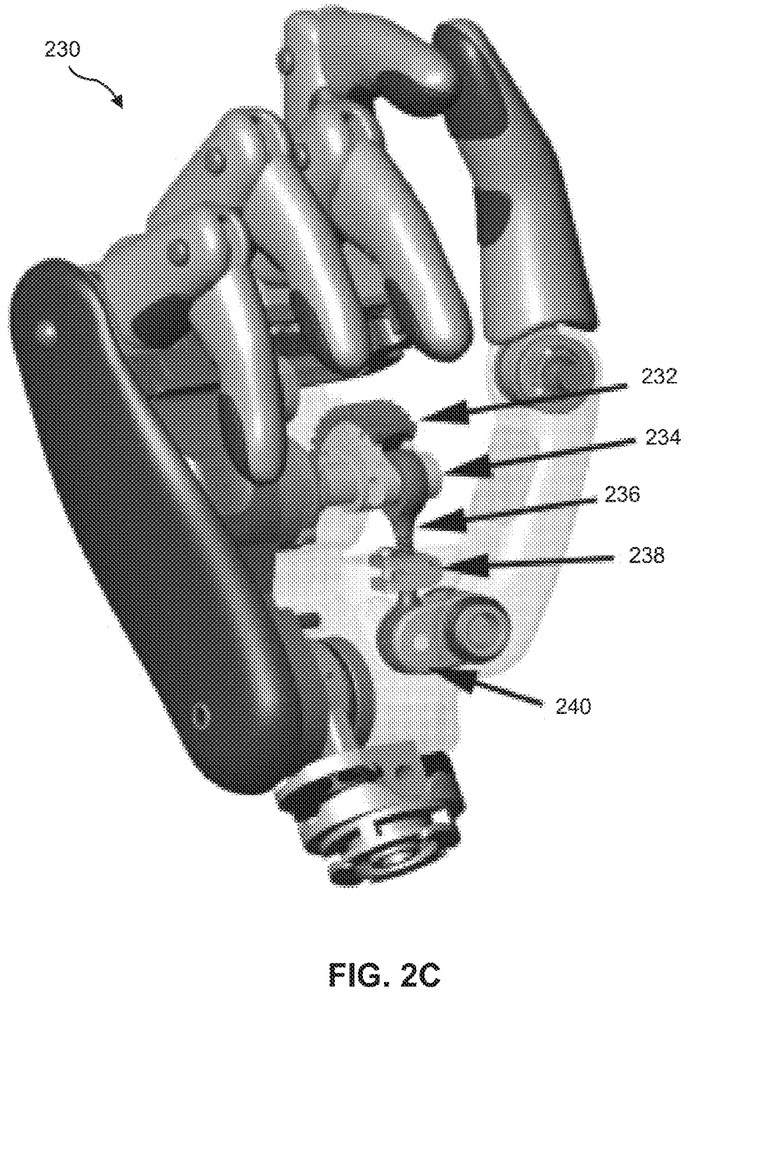

FIGS. 2A-2C show an exemplary thumb drive mechanism included in a hand prosthesis system 210, 220 and 230. The hand prosthesis system 210 in FIG. 2A may include a thumb drive mechanism 211 comprising a drive crank 212, a rod-end bearing 214, a gear 216, and/or a driven crank 218. In one example, the gear 216 in the thumb drive mechanism 211 may be in communication with the drive crank 212, which in turn may be coupled with a spherical bearing on a first end of the rod-end bearing 214, where the rod-end bearing 214 may drive a link to another spherical bearing on a second end of the rod-end bearing 214. As a result, driving the drive crank 212 in a first direction (e.g., clockwise) may cause the thumb member 213 to actuate and perform a pinch motion. Driving the drive crank 212 in a second direction (e.g., counter clockwise) may cause the thumb member 213 to actuate and perform a release motion. In addition, the thumb drive mechanism can include a motor (i.e., an electric motor) mounted within a hand chassis of the hand prosthesis system 210, 220 and 230, the motor being operable to drive the drive crank 212 via the gear 216. In one example, the motor may be in communication with a first stage gear that is engaged with a second stage gear attached to the drive crank 212. Thus, when power is supplied to the motor, the motor drives the first stage gear which in turn drives the second stage gear.

The described configuration of the hand prosthesis system 210 in FIG. 2A may allow the thumb member 213 to be passively positioned laterally to the finger members 215. Alternatively, the thumb member 213 may be passively positioned opposing the finger members 215. As illustrated in FIG. 2B, the hand prosthesis system 220 may include a thumb axis of rotation 222 angled forward from a hand chassis axis 226 to a predefined angle 224. In one example configuration, the predefined angle 224 may be configured to an angle within a range of about 20 degrees to 30 degrees. In a specific example, the predefined angle 224 may be configured to about 26 degrees. By angling the thumb axis of rotation 222 forward from the hand chassis axis 226 by the predefined angle 224, the thumb member 228 rotates from a lateral position to an opposing position with relatively little translation. In addition, angling the thumb axis of rotation 222 by the predefined angle 224 may allow the thumb member 228, when actuated, to be positioned near the fingertips of the finger members for optimal grasp.

FIG. 2C illustrates an additional view of the hand prosthesis system 230, including a gear 232, a drive crank 234, a rod-end bearing 236, a load cell 238, and/or a driven crank 240. In one example configuration, the load cell 238 may be situated between a first casing and a second casing of the rod-end bearing 236. The load cell 238 may be configured to detect a load amount being applied by the system. For example, the load cell 238 may be a strain gauge load cell configured to detect when a force applied by the drive crank 234 via a motor may be at, or nearing, a force (i.e., load amount) that exceeds a predetermined threshold.

Figure 3:
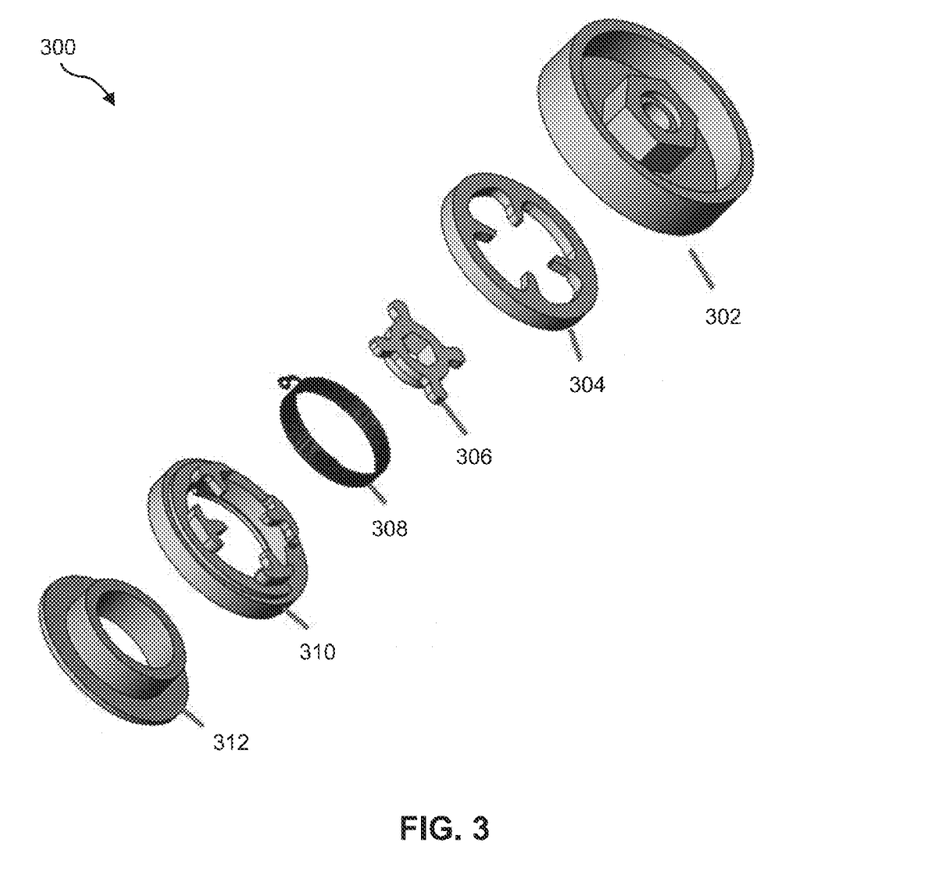
FIG. 3 illustrates an exploded view of an exemplary backlock included in the hand prosthesis system.

FIG. 3 illustrates an exploded view of an exemplary backlock 300 included in the hand prosthesis system. In some example configurations, the backlock 300 may be included in a thumb drive mechanism of an externally-powered hand prosthesis system. The backlock 300 may allow input torque (e.g., torque produced by a motor) in either direction (i.e., forward or reverse) to be transferred through the thumb drive mechanism to a thumb member causing the thumb member to actuate. For example, the backlock 300 may allow torque to be applied to an input (e.g., a drive cog 306) of the backlock 300 thereby unwinding a spring 308 from around a core element 312. Once the spring 308 is unwound from around the core element 312, the thumb drive mechanism may be free from the restraint of the spring 308 and can therefore drive an associated thumb member (i.e., cause the thumb member to perform a pinch/grasp motion or release motion). Further, the backlock 300 may allow output torque (e.g., back pressure produced by input torque) to cause the spring 308 to wrap around the core element 312 thereby restraining the thumb drive mechanism and preventing the movement of the thumb member. As a result, grasped objects by the hand prosthesis system may remain secure when electrical power is terminated to a motor of the thumb drive mechanism, thereby saving battery life.

As illustrated in FIG. 3, the backlock 300 may include an output element 302, an outer spring driver 304, a drive cog 306, a spring 308, an inner spring driver 310, and/or a core element 312. In some example configurations, the output element 302 may be towards the top of the backlock 300, and the core element 312 may be towards the bottom of the backlock 300. Additionally, the output element 302 may cause output torque to act on the wrap sides of the inner spring driver 310 and the outer spring driver 304. In one example, the inner spring driver 310 may act on the spring 308 in the direction towards the bottom of the backlock 300, while the outer spring driver 304 acts on the spring 308 in the direction towards the top of the backlock 300. In another example, the spring 308 may provide the necessary force to wrap around the core element 312, or in the contrary, the spring 308 may provide a lack of force to unwrap around the core element 312.

Figure 4A:
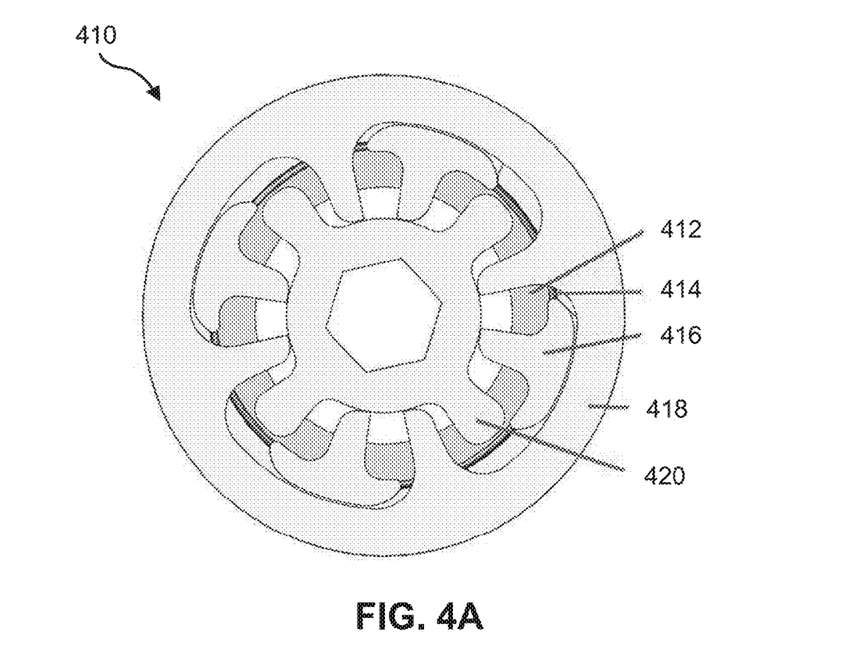
FIGS. 4A and 4B illustrate a top view of an exemplary backlock included in the hand prosthesis system.
Figure 4B:
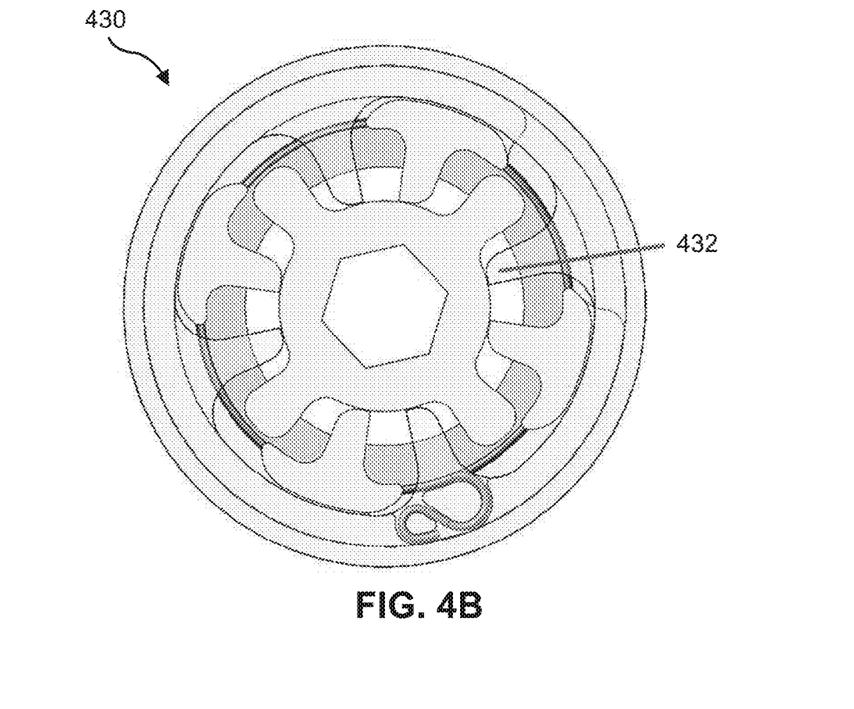

FIGS. 4A and 4B illustrate a top view of the backlock 410 and 430 included in a hand prosthesis system. FIGS. 4A and 4B illustrate the backlock 410 and 430 in an unwrapped position, where an output element may be hidden. FIG. 4A includes a core element 412, a spring 414, an inner spring driver 416, an outer spring driver 418, and/or a drive cog 420. FIG. 4B further illustrates that the outer spring driver 432 may be transparent.

In one example configuration, an input of the backlock 410 and 430 may be a link element, shaft element or some other input element that is in communication with the drive cog 420. In an example of the backlock 410 and 430, an input may be configured such that when torque is applied to the input of the backlock 410 and 430, the torque causes the drive cog 420 to unwrap the spring 414 from around the core element 412. More specifically, torque applied to the input of the backlock 410 and 430 cause the drive cog 420 to rotate and engage the outer spring driver 418. The drive cog 420 and the outer spring driver 418 then rotate together and engage the inner spring driver 416, thereby unwrapping the spring 414 from around the core element 412.

In another example, the output element of the backlock 410 and 430 may be configured to enable the spring 414 to wrap around the core element 412 when torque is applied to the output element. More specifically, the output element can engage the drive cog 420 thereby rotating the drive cog 420 until the inner spring driver 416 is engaged by the drive cog 420. The output element and the inner spring driver 416 then rotate together until the outer spring driver 418 is engaged by the output element and the inner spring driver 416, thereby allowing the spring 414 to wrap around the core element 412.

Figure 5:
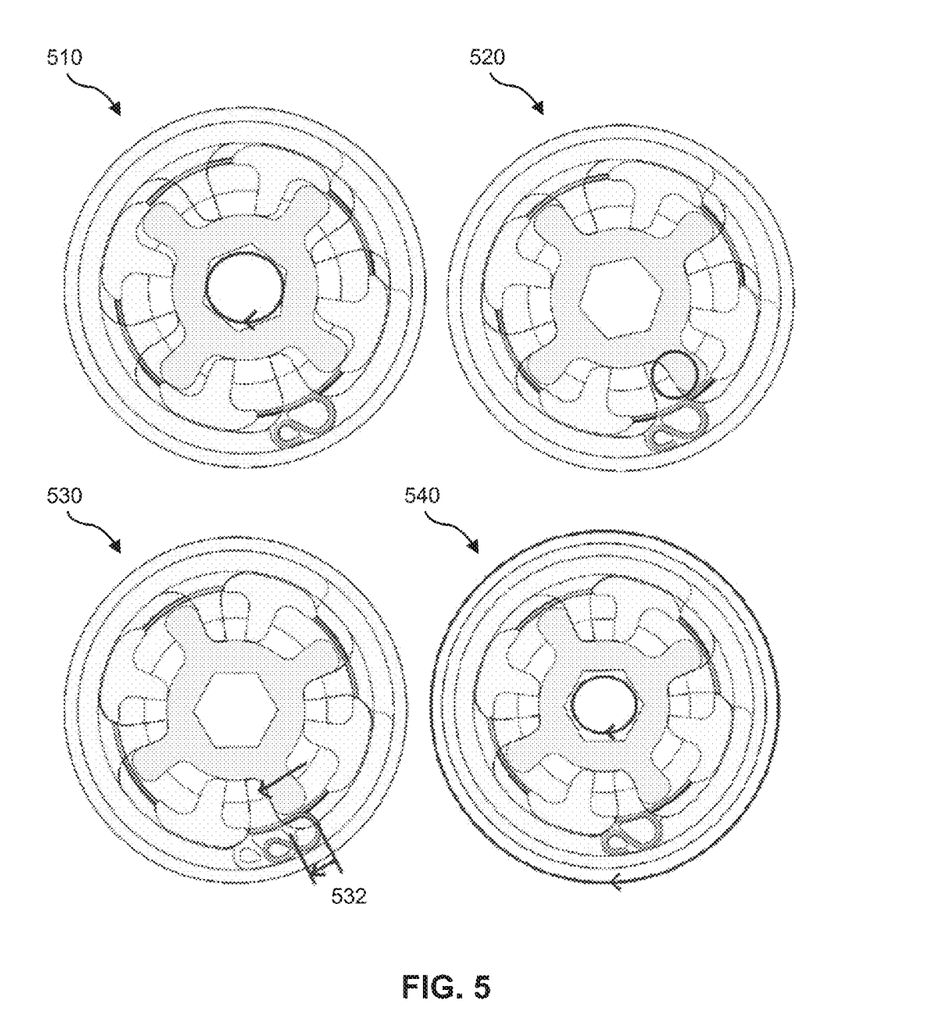
FIG. 5 illustrates a top view of an exemplary backlock included in the hand prosthesis system.

FIG. 5 illustrates a top view of the backlock 300 shown in FIG. 3 that can be included in a hand prosthesis system. In some embodiments, torque may apply to the drive cog 420 in the clockwise direction, as illustrated in 510. As a result, the drive cog 420 may rotate until hitting the outer spring driver 418, as illustrated in 520. Subsequent to the drive cog 420 hitting the outer spring driver 418, both the drive cog 420 and the outer spring driver 418 may rotate together until hitting the inner spring driver 416. At this point, the spring 414 may be unwrapped by the length 532 that the outer spring driver 418 travels before hitting the inner spring driver 416, as illustrated in 530. The unwrapping of the spring 414 can be enough to clear the core element 412 of the spring 414, thereby allowing the torque from the input (i.e., via the drive cog 306) of the backlock 300 to transfer to the output (i.e., via the output element 302) of the backlock 300. In some examples, the torque may transfer from the input to the output with a relatively small amount of drag. When the outer spring driver 418 proceeds to hit the inner spring driver 416, both the outer spring driver 418 and the inner spring driver 416 may rotate with the input torque, as illustrated in 540.

Figure 6A:
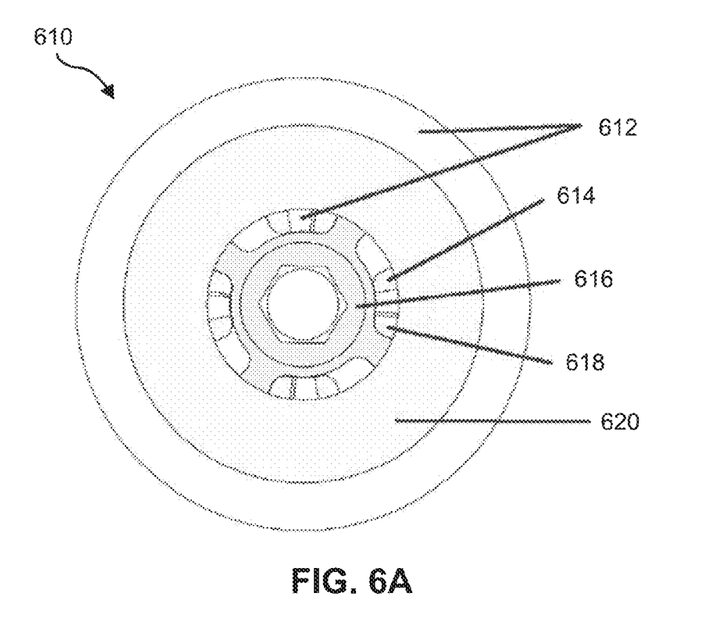
FIGS. 6A and 6B illustrate a bottom view of an exemplary backlock included in the hand prosthesis system.
Figure 6B:
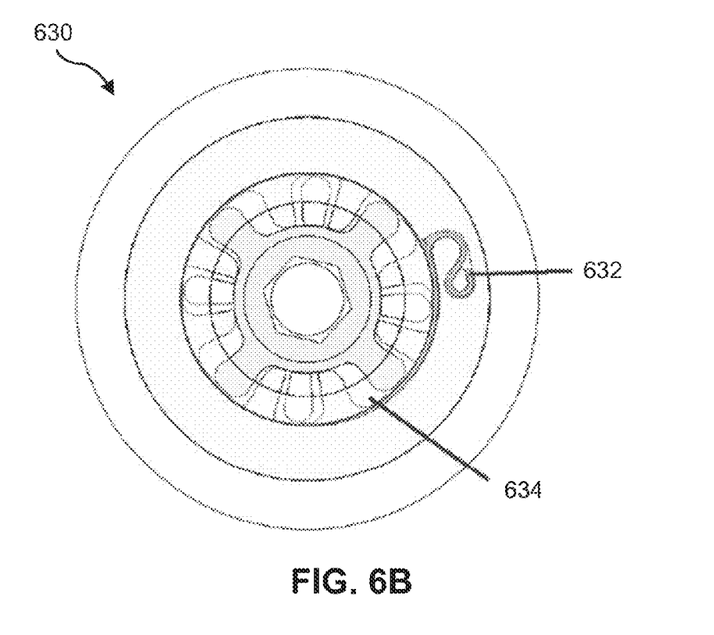

FIGS. 6A and 6B illustrate a bottom view of the backlock 300 included in the hand prosthesis system. FIGS. 6A and 6B illustrate the backlock 610 and 630 in a wrapped position. FIG. 6A includes an output element 612, an inner spring driver 614, a drive cog 616, an outer spring driver 618, and/or a core element 620. FIG. 6B may include a spring 632. In addition, FIG. 6B also illustrates that the core element 620 may be transparent 634. In some example configurations, applying torque to the output may result in the output element 612 being moved, thereby acting on the inner spring driver 614. In other example configurations, applying torque to the output may result in the output element 612 being moved, thereby acting on the outer spring driver 618. In some example configurations, the output element 612 may act on the inner spring driver 614 counter-clockwise when viewed looking down on the core element 620. In other examples, the output element 612 may act on the outer spring driver 618 clockwise when viewed looking down on the core element 620.

Figure 7:
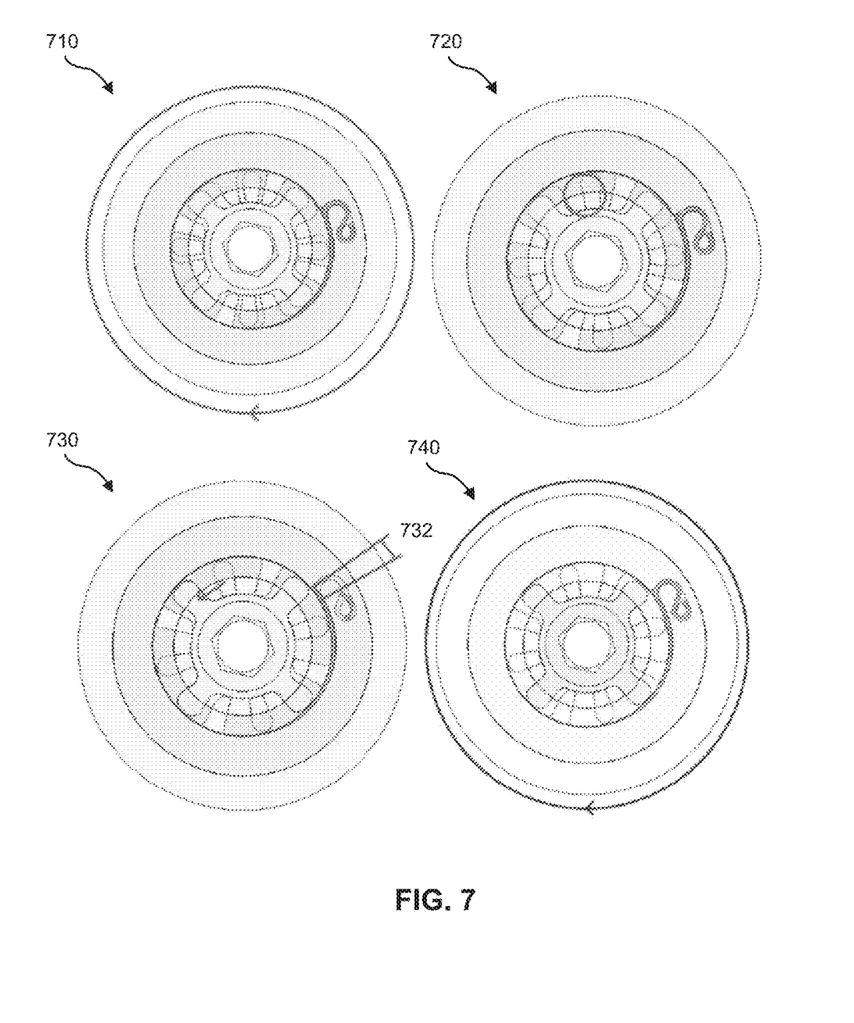
FIG. 7 illustrates a bottom view of an exemplary backlock included in the hand prosthesis system.

FIG. 7 illustrates a bottom view of the backlock 300 included in a hand prosthesis system. In some examples, torque may be applied to the output element 612 in the counter-clockwise direction, as illustrated in 710. As a result, the drive cog 616 may rotate until hitting the inner spring driver 614, as illustrated in 720. Subsequent to the drive cog 616 hitting the inner spring driver 614, both the drive cog 616 and the inner spring driver 614 may rotate together until hitting the outer spring driver 618. At this point, the spring 632 may be wrapped by the length 732 that the inner spring driver 614 travels before hitting the outer spring driver 618, as illustrated in 730.

Continuing with FIG. 7, the wrapping of the spring 632 may be enough for the spring 632 to firmly hold the core element 620. In other words, the wrapping of the spring 632 may be enough for the spring 632 to grip the core element 620. In some examples, the firm hold on the core element 620 may provide a calculated torque. In one example, the spring 632 may be a torsion spring providing a torque rating within a range of about 20 inch ounces of torque to about 30 inch ounces of torque. In a specific example, the calculated torque may be about 25 in-ozs. In other examples, the calculated torque may be a different numerical value. In general, the spring 632 may begin to lose its hold (e.g., slip) on the core element 620 if a torque greater than the calculated value is applied to the output element 612, thus, providing an overload protection for a prosthetic hand drive mechanism. Thus, a high load applied to a thumb member may result in the backlock slipping, rather than breaking. In some examples, a torque greater than 25 in-oz. applied to the output 612 may cause the spring 632 to lose its hold on the core element 620. As a result of the spring 632 slipping on the core element 620, the backlock rotates, as illustrated in 740.

Figure 8:
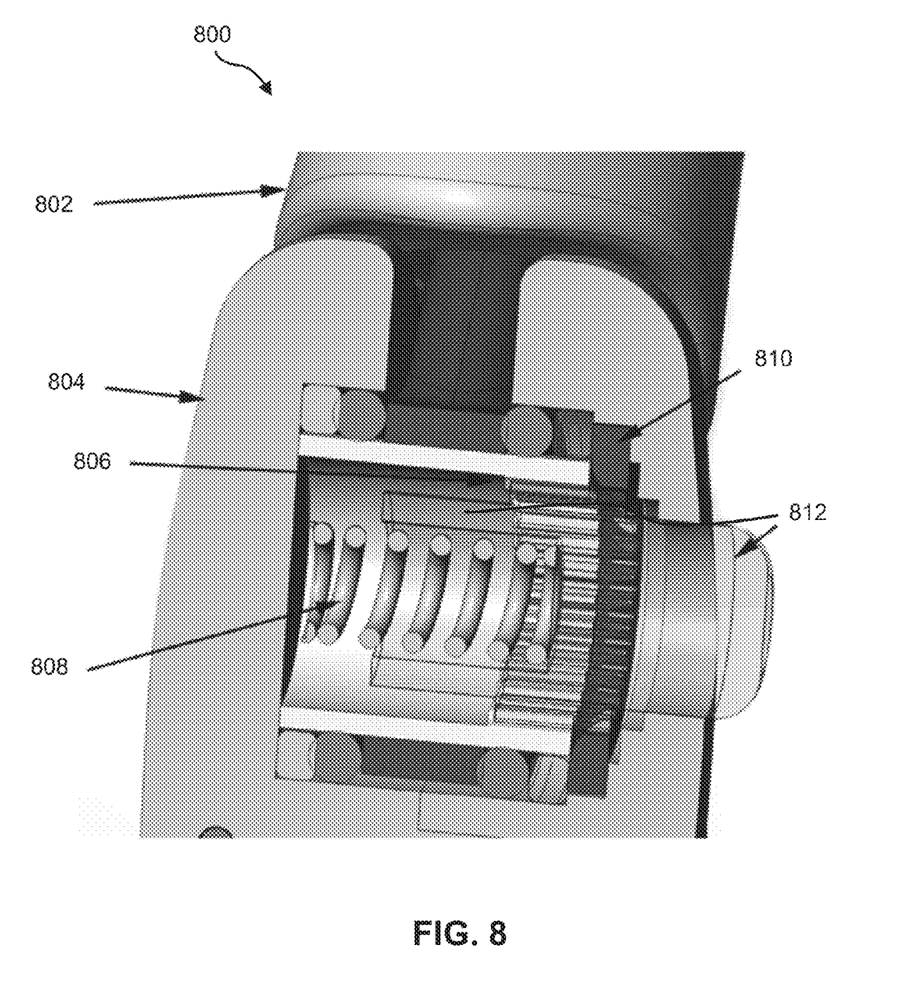
FIG. 8 illustrates an exemplary gear lock mechanism included in the hand prosthesis system.

FIG. 8 illustrates an exemplary gear lock mechanism 800 that may be included in the hand prosthesis system. In an example configuration, the gear lock mechanism 800 may be implemented in a finger joint. In a specific example, the gear lock mechanism 800 may be included in an externally-powered hand and wrist prosthetic system. The gear lock mechanism 800 includes a distal finger link 802, a proximal finger link 804, a first internal gear 806, a spring 808, a second internal gear 810, and/or a button and an external gear 812 with an attached button. In an example, the first internal gear 806 may be attached to the distal finger link 802, while the second internal gear 810 may be attached to the proximal finger link 804. In some examples, the first internal gear 806 and the second internal gear 810 may be mounted by means of a compliant member, thereby providing natural compliance and/or springiness to the joint. This springiness may also allow for benefits that result from having a "series-elastic-element" in the drive when doing force control. In some examples, the gear lock mechanism 800 may include an external gear that is coupled to a lock button 812. For example, the external gear coupled to the lock button 812 may be used to bridge between the first internal gear 806 and the second internal gear 810, thereby locking the finger joint. In some examples, the gear lock mechanism 800 may include a spring 808. For example, the spring 808 may be used to return the button 812 with the external gear to a locked position. Alternatively, the spring 808 may be used to return the button 812 to an unlocked position. In other embodiments, the spring 808 may return the first and second internal gears 806 and 810 to a locked position. In some examples, the first internal gear 806 attached to the distal finger link 802 may be coupled to the link via a servo clamp. In other examples, the second internal gear 810 attached to the proximal finger link 804 may be coupled to the link via a servo clamp. The servo clamp may slip when overloaded, thereby providing an overload protection for the gear locking mechanism.

Figure 9:
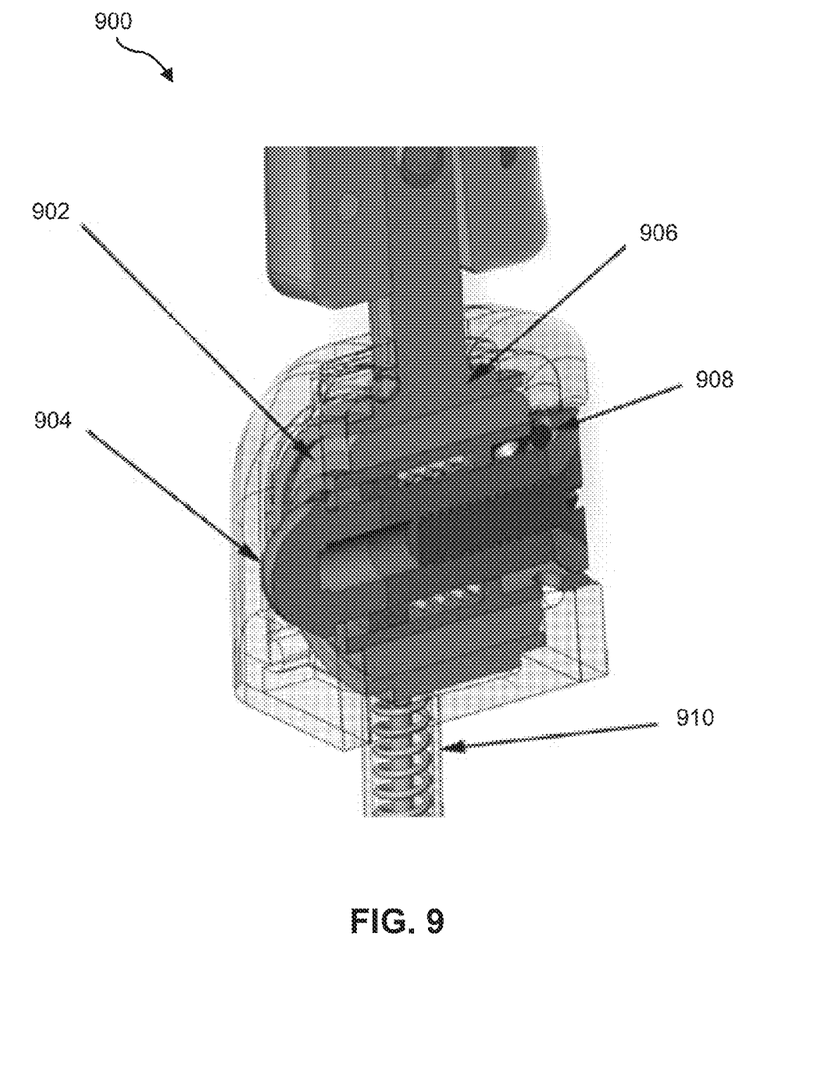
FIG. 9 illustrates an exemplary adaptive gripping joint included in the hand prosthesis system.

FIG. 9 illustrates an adaptive gripping joint 900 that may be included in a hand prosthesis system. The adaptive gripping joint 900 may include a one-way bearing 902, an unlock button 904, a servo clamp 906, a ball locking mechanism 908, and/or a spring 910. In some embodiments, the unlock button 904 may include a spring return, while the spring 910 may extend the distal link when unlocked. In some embodiments, the adaptive gripping joint 900 may allow the fingers to passively adapt to a variety of different shaped objects. For example, the adaptive gripping joint 900 may allow a prosthetic joint to flex into a desired position. In some examples, the one-way bearing 902 may allow the finger to flex against a grasped object. In other examples, the one-way bearing 902 may allow the finger to flex into a grasped object. In one example configuration, the one-way bearing 902 allows the finger to not extend until the ball locking mechanism 908 is disengaged. For example, the ball locking mechanism 908 may be disengaged by pressing the unlock button 904, wherein the unlock button 904 may be located on the side of the hand.

The described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

What is claimed is:

1. A backlock for a prosthetic hand drive mechanism, comprising:

a spring, wherein the spring wraps around a core element when torque is applied to an output of the backlock, and the spring unwraps around the core element when torque is applied to an input of the backlock;

an inner spring driver configured to act on a first direction of the spring;

an outer spring driver configured to act on a second direction of the spring;

a drive cog, wherein the drive cog causes an input torque to act on unwrapped sides of the inner spring driver and the outer spring driver, wherein the drive cog is configured to unwrap the spring from around the core element when torque is applied to the drive cog, whereby the drive cog is configured to rotate and engage the outer spring driver such that the drive cog and the outer spring driver rotate together and engage the inner spring driver; and an output element, wherein the output element causes an output torque to act on wrapped sides of the inner spring driver and the outer spring driver.

2. A backlock for a prosthetic hand drive mechanism as in claim 1, wherein the spring further comprises a torsion spring providing torque rating within a range of about 20 inch ounces of torque to about 30 inch ounces of torque.

3. A backlock for a prosthetic hand drive mechanism as in claim 1, further comprising configuring the spring to provide an overload protection for the prosthetic hand drive mechanism, whereby the spring is wrapped around the core element enabling the spring to slip on the core element when a torque rating is exceeded.

4. A backlock for a prosthetic hand drive mechanism as in claim 1, further comprising configuring the output element to enable the spring to wrap around the core element when torque is applied to the output element, whereby the output element engages the drive cog rotating the drive cog until the inner spring driver is engaged by the drive cog, the output element and the inner spring driver rotate together until the outer spring driver is engaged by the output element and the inner spring driver.

* * * * *